United States Patent [19]

Farge et al.

[11] 4,189,480
[45] Feb. 19, 1980

[54] ISOQUINOLINE DERIVATIVES

[75] Inventors: Daniel Farge, Thiais; Alain Jossin, Saint Cloud; Gerard Ponsinet, Sucy-en-Brie; Daniel Reisdorf, Thiais, all of France

[73] Assignee: Rhone-Poulenc Industries, Paris, France

[21] Appl. No.: 958,617

[22] Filed: Nov. 8, 1978

[30] Foreign Application Priority Data

Nov. 10, 1977 [FR] France .................................. 77 33890
Aug. 9, 1978 [FR] France .................................. 78 23469

[51] Int. Cl.² .................... C07D 279/08; A61K 31/54
[52] U.S. Cl. ........................................ 424/246; 544/32
[58] Field of Search ........................... 544/32; 424/246

[56] References Cited
U.S. PATENT DOCUMENTS

| | | | |
|---|---|---|---|
| 4,064,247 | 12/1977 | Farge et al. | 424/258 |
| 4,147,862 | 4/1979 | Hayami et al. | 544/32 |
| 4,153,698 | 5/1979 | Farge et al. | 424/258 |
| 4,153,699 | 5/1979 | Farge et al. | 424/258 |

Primary Examiner—John M. Ford
Attorney, Agent, or Firm—Stevens, Davis, Miller & Mosher

[57] ABSTRACT

Isoquinoline derivatives of the formula:

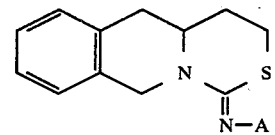

wherein A represents pyrid-3-yl, isoquinol-5-yl or a 3-alkylisoquinol-5-yl radical in which the alkyl moiety contains 1 to 10 carbon atoms, are new compounds, possessing useful pharmacological properties. They are particularly valuable as analgesic, anti-inflammatory and antipyretic agents.

10 Claims, No Drawings

ISOQUINOLINE DERIVATIVES

This invention relates to new therapeutically useful isoquinoline derivatives, to processes for their preparation and pharmaceutical compositions containing them.

The new isoquinoline derivatives of the present invention are those of the general formula:

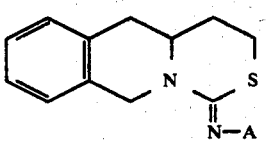  I wherein the symbol A represents a pyrid-3-yl or isoquinol-5-yl radical or a 3-alkylisoquinol-5-yl radical in which the alkyl moiety contains 1 to 10 carbon atoms in a straight or branched chain, and acid addition salts thereof.

The compounds of general formula I can exist in (R) and (S) forms and the invention includes both such forms and mixtures thereof.

According to a feature of the present invention, the isoquinoline derivatives of general formula I are prepared by the process which comprises the cyclisation of a 1,2,3,4-tetrahydroisoquinoline of the general formula:

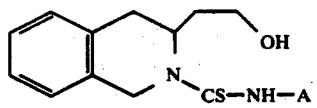  II wherein A is as hereinbefore defined. the cyclisation can be carried out either directly by heating in an acid medium, in which case the reaction is advantageously carried out at a temperature between 90° and 100° C. in an aqueous solution of an inorganic acid, e.g. in hydrochloric acid, or by the action of methanesulphonyl chloride or tosyl chloride in an organic solvent, such as pyridine, at a temperature of about 20° C., after which the intermediate formed of the general formula:

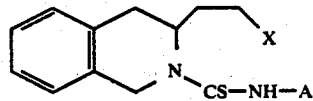  III (wherein A is as hereinbefore defined, and X represents the methanesulphonyloxy or tosyloxy radical) is heated at a temperature between 60° and 120° C. in dimethylformamide.

The 1,2,3,4-tetrahydroisoquinolines of general formula II can be obtained by the reaction of an isothiocyanate of the general formula:

  S=C=N-A  IV (wherein A is as hereinbefore defined) with 3-(2-hydroxyethyl)-1,2,3,4-tetrahydroisoquinoline. The reaction is generally carried out in an organic solvent such as an alcohol, e.g. ethanol, at a temperature between 20° and 60° C. 3-Isothiocyanatopyridine can be obtained in accordance with the method described by J. C. Jochims, Chem. Ber., 101, 1746 (1968).

5-Isothiocyanatoisoquinoline can be prepared from 5-aminoisoquinoline in accordance with the method described in French Patent Publication 2320098 or British Patent Specification 1503091.

The isothiocyanates of general formula IV wherein A is a 3-alkylisoquinol-5-yl radical, in which the alkyl moiety contains 1 to 10 carbon atoms in a straight or branched chain, can be obtained by the action of carbon disulphide on a 5-aminoisoquinoline of the general formula:

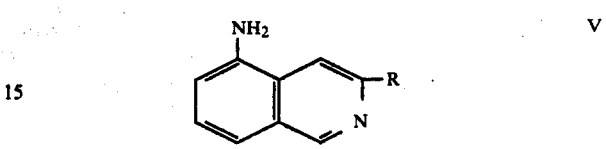  V (wherein R represents a straight- or branched-chain alkyl radical containing 1 to 10 carbon atoms) followed by the addition of dicylclohexylcarbodiimide. The condensation is generally carried out in the presence of a base such as a tertiary amine, e.g. triethylamine. The reaction is advantageously carried out in an organic solvent, such as pyridine, at a temperature between −10° and 25° C.

The 5-aminoisoquinolines of general formula V, wherein R represents a striaight- or branched-chain alkyl radical containing 1 to 10 carbon atoms, can be obtained from a 3-alkylisoquinoline of the general formula:

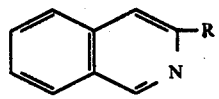  VI (wherein R is as hereinbefore defined) by applying the method of N.P. Buu-Hoï et al., J. Chem. Soc., 3924 (1964).

The isoquinolines of general formula VI can be obtained in accordance with the method described by J. Murakoshi et al., Yakugaku Zasshi, 79, 1578 (1959) or in accordance with the method described by F. Damerow, Ber., 27, 2232 (1894). 3-(2-Hydroxyethyl)-1,2,3,4-tetrahydroisoquinoline can be prepared from 3-hydroxymethyl-1,2,3,4-tetrahydroisoquinoline in accordance with the method described by T. A. Crabb et al., J. C. S. Perkin II, 370 (1977).

3-Hydroxymethyl-1,2,3,4-tetrahydroisoquinoline can be prepared from phenylalanine in accordance with the method described by S. Yamada and T. Kunieda, Chem. Pharm. Bull., 15, 490 (1967).

When L-phenylalanine is used, the isoquinoline product of general formula I is obtained in the (S) form.

When D-phenylalanine is used, the isoquinoline product of general formula I is obtained in the (R) form.

When D,L-phenylalanine is used, the isoquinoline product of general formula I is obtained in the (RS) form.

The isoquinoline derivatives of general formula I can also be obtained by the process which comprises the reaction of an amine of the general formula:

  A—NH₂  VII (wherein A is as hereinbefore defined) with a salt of the general formula:

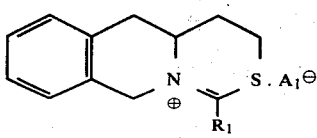
VIII wherein $R_1$ represents a chlorine atom, an alkylthio radical containing 1 to 4 carbon atoms (preferably methylthio), or a benzylthio radical, and $A_1^\ominus$ represents an anion, such as a chloride, iodide, sulphate, tetrafluoroborate or fluorosulphonate ion. When $R_1$ represents a chlorine atom, $A_1^\ominus$ represents a chloride ion. When $R_1$ represents an alkylthio or benzylthio radical, $A_1^\ominus$ represents an iodide, sulphate, tetrafluoroborate or fluorosulphonate ion.

When $R_1$ represents a chlorine atom and $A_1^\ominus$ represents a chloride ion, the reaction is preferably carried out in an organic solvent, such as acetonitrile, in the presence of an alkaline condensing agent, such as triethylamine, at a temperature of about 20° C.

When $R_1$ represents an alkylthio or benzylthio radical and $A_1^\ominus$ represents an iodide, sulphate, tetrafluoroborate or fluorosulphonate ion, the reaction is preferably carried out in a basic organic solvent, such as pyridine, at a temperature between 30° and 50° C.

The salt of the general formula VIII wherein $R_1$ represents a chlorine atom and $A_1^\ominus$ represents a chloride ion can be obtained by the reaction of a chlorinating agent, such as phosgene, phosphorus pentachloride, thionyl chloride or oxalyl chloride, on 1,6,11,11a-tetrahydro[1,3-thiazino][3,4-b]-isoquinoline-4-thione of the formula:

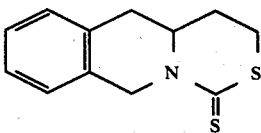
IX

The reaction is generally carried out in an organic solvent or in a mixture of organic solvents, such as a mixture of toluene and tetrahydrofuran, at a temperature between 0° and 70° C.

The salts of general formula VIII wherein $R_1$ represents an alkylthio or benzylthio radical and $A_1^\ominus$ represents an iodide, sulphate, tetrafluoroborate or fluorosulphonate ion can be obtained by the action of a reactive ester of the general formula:

$$R_2-A_1 \qquad \qquad X$$

(wherein $R_2$ represents an alkyl radical containing 1 to 4 carbon atoms or a benzyl radical, and $A_1$ represents the residue of a reactive ester such as an iodine atom or an alkoxysulphonyloxy radical), or by the action of triethyloxonium tetrafluoroborate or methyl fluorosulphonate, on the compound of formula IX. The reaction is generally carried out, optionally in the presence of an organic solvent, such as dichloromethane, chloroform or dichloroethane, at a temperature of about 20° C. 1,6,11,11a-Tetrahydro[1,3-thiazino][3,4-b]-isoquinoline-4-thione can be prepared by reacting 3-(2-hydroxyethyl)-1,2,3,4-tetrahydroisoquinoline successively with carbon disulphide in the presence of triethylamine and then with methanesulphonyl chloride or tosyl chloride, followed by cyclisation of the intermediate obtained.

The carbon disulphide is generally reacted with the tetrahydroisoquinoline in the presence of a base such as a tertiary amine, e.g. triethylamine.

The successive reaction of carbon disulphide and then methanesulphonyl chloride or tosyl chloride is advantageously carried out in an organic solvent such as pyridine, at a temperature between −10° and 20° C.

The cyclisation of the intermediate is generally carried out by heating in an organic solvent, such as dimethylformamide or in a mixture of organic solvents (for example dimethylformamide and pyridine), at a temperature between 50° and 100° C. It is not necessary to isolate the intermediate in order to perform this cyclisation.

The isoquinoline derivatives of general formula I may be converted by known methods into acid addition salts. (By the term "known methods" is meant methods heretofore used or described in the chemical literature). The acid addition salts may be obtained by reacting the isoquinoline derivatives with acids in appropriate solvents. As organic solvents there may be used alcohols, ketones, ethers or chlorinated hydrocarbons. The salt which is formed is precipitated, if necessary after concentration of the solution, and is isolated by filtration or decantation.

The isoquinoline derivatives of general formula I and/or their acid addition salts can optionally be purified by physical methods such as crystallisation or chromatography.

The isoquinoline derivatives of general formula I and their acid addition salts possess useful pharmacological properties. They are particular active as analgesic, anti-inflammatory and antipyretic agents.

The analgesic activity manifests itself in mice at doses between 0.25 and 100 mg/kg animal body weight, administered orally, using the technique of Siegmund et al., Proc. Soc. Exp. Biol. Med., 95, 729 (1957).

The anti-inflammatory activity manifests itself in rats at doses between 0.25 and 100 mg/kg animal body weight, administered orally, using the technique of K. F. Benitz and L. M. Hall, Arch. Int. Pharmacodyn., 144, 185 (1963).

The antipyretic activity manifests itself in rats at doses between 0.25 and 50 mg/kg animal body weight, administered orally, using the technique of J. J. Loux et al., Toxicol. Appl. Pharmacol., 22, 674 (1972).

Furthermore, the isoquinoline derivatives of the invention are of very low toxicity. Their acute toxicity in mice is between 500 and 5000 mg/kg animal body weight, administered orally.

Of particular interest are those isoquinoline derivatives of general formula I wherein the symbol A represents an isoquinol-5-yl radical or a 3-alkylisoquinol-5-yl radical in which the alkyl moiety contains 1 to 8 carbon atoms in a straight chain. Of outstanding interest are those compounds wherein A represents an isoquinol-5-yl or 3-methylisoquinol-5-yl radical and, in particular, (RS)-4-(isoquinol-5-ylimino)-1,6,11,11a-tetrahydro[1,3-thiazino][3,4-b]isoquinoline and (RS)-4-[(3-methylisoquinol-5-yl)imino]-1,6,11,11a-tetrahydro[1,3-thiazino][3,4-b]isoquinoline.

For therapeutic purposes the isoquinoline derivatives of general formula I are employed as such or in the form of pharmaceutically acceptable salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllinacetates, salicylates, phenolphthalinates and methylene-bis-β-hydroxynaphthoates) so that the beneficial physiological properties inherent in the bases are not vitiated by side-effects ascribable to the anions.

The following Examples illustrate the preparation of the new isoquinoline derivatives of the present invention.

EXAMPLE 1

(RS)-3-(2-Hydroxyethyl)-N-(pyrid-3-yl)-1,2,3,4-tetrahydroisoquinoline-2-carbothioamide (4.7 g) is heated in 6 N hydrochloric acid (50 cc) for 30 minutes at 100° C. After cooling, the solution is rendered alkaline by addition of 10 N sodium hydroxide solution (33 cc); extraction is then carried out with methylene chloride (3×50 cc). The organic extracts are combined, washed with water (50 cc) and dried over magnesium sulphate. After filtration, the filtrate is evaporated to dryness at 40° C. under reduced pressure (40 mm Hg). The oily residue is chromatographed on silica gel (40 g) contained in a column 2 cm in diameter, elution being carried out successively with methylene chloride (1000 cc) and a mixture (98-2) of methylene chloride and methanol (2500 cc), the eluate being collected in fractions (100 cc). Fractions 10 to 35 are combined and evaporated to dryness under reduced pressure (0.5 mm Hg) at 80° C.

(RS)-4-(Pyrid-3-ylimino)-1,6,11,11a-tetrahydro[1,3-thiazino][3,4-b]isoquinoline (3.8 g) is thus obtained in the form of an oil. It is dissolved in absolute ethanol (18 cc), fumaric acid (1.7 g) is added to the solution and the mixture is heated under reflux until the solid has dissolved. On cooling, white crystals are deposited which are isolated by filtration and recrystallised from ethanol (40 cc). (RS)-4-(Pyrid-3-ylimino)-1,6,11,11a-tetrahydro[1,3-thiazino][3,4-b]-isoquinoline (2.7 g) is thus obtained in the form of the neutral fumarate which melts at 150° C.

(RS)-3-(2-Hydroxyethyl)-N-(pyrid-3-yl)-1,2,3,4-tetrahydroisoquinoline-2-carbothioamide can be prepared in the following manner:

3-Isothiocyanatopyridine (2.6 g) is added to a solution of (RS)-3-(2-hydroxyethyl)-1,2,3,4-tetrahydroisoquinoline (3.3 g) in ethanol (40 cc). A white precipitate forms after 5 hours; stirring is continued for 12 hours at a temperature of about 20° C. The crystals which have appeared are filtered off and washed with diethyl ether (2×5 cc). (RS)-3-(2-Hydroxyethyl)-N-(pyrid-3-yl)-1,2,3,4-tetrahydroisoquinoline-2-carbothioamide (4.7 g), melting at 174° C., is thus obtained.

3-Isothiocyanatopyridine can be prepared in accordance with the method described by J. C. Jochims, Chem. Ber., 101, 1746 (1968).

EXAMPLE 2

By following the procedure of Example 1 but starting with (RS)-3-(2-hydroxyethyl)-N-(isoquinol-5-yl)-1,2,3,4-tetrahydroisoquinoline-2-carbothioamide (9.8 g) in 6 N hydrochloric acid (100 cc), (RS)-4-(isoquinol-5-ylimino)-1,6,11,11a-tetrahydro[1,3-thiazino][3,4-b]isoquinoline (6.3 g), melting at 151° C., is obtained.

(RS)-3-(2-Hydroxyethyl)-N-(isoquinol-5-yl)-1,2,3,4-tetrahydroisoquinoline-2-carbothioamide (m.p. 185° C.) can be prepared from (RS)-3-(2-hydroxyethyl)-1,2,3,4-tetrahydroisoquinoline and 5-isothiocyanatoisoquinoline by operating under the conditions described in Example 1.

5-Isothiocyanatoisoquinoline can be prepared from 5-aminoisoquinoline in accordance with the method described in French Patent Publication 2320098 or British Patent Specification 1503091.

EXAMPLE 3

(RS)-4-Methylthio-1,6,11,11a-tetrahydro[1,3-thiazino][3,4-b]isoquinolinium iodide (0.67 g) is added to a solution of 5-aminoisoquinoline (0.42 g) in pyridine (20 cc) and the mixture is heated at 40° C. for 48 hours. It is then evaporated to dryness under reduced pressure (25 mm Hg) at 50° C. The residue is dissolved in a mixture of methylene chloride (50 cc) and 2 N sodium hydroxide solution (20 cc). The organic phase is decanted, washed with water (2×30 cc), dried over magnesium sulphate, filtered and then concentrated to dryness under reduced pressure (40 mm Hg) at 30° C. The residue is chromatographed on silica gel (6 g) contained in a column 0.7 cm in diameter, elution being carried out with methylene chloride and the eluate being collected in fractions (30 cc). Fractions 3 to 5 are combined and evaporated to dryness under reduced pressure (40 mm Hg) at 30° C. (RS)-4-(Isoquinol-5-ylimino)-1,6,11,11a-tetrahydro[1,3-thiazino][3,4-b]isoquinoline (0.14 g) is thus obtained in the form of white crystals melting at 150° C.

(RS)-4-Methylthio-1,6,11,11a-tetrahydro[1,3-thiazino][3,4-b]isoquinolinium iodide can be prepared in the following manner:

(RS)-1,6,11,11a-Tetrahydro[1,3-thiazino][3,4-b]isoquinoline-4-thione (0.67 g) is dissolved in methyl iodide (20 cc). After 15 hours at a temperature of about 20° C., the mixture is concentrated under reduced pressure (20 mm Hg) at 20° C. (RS)-4-Methylthio-1,6,11,11a-tetrahydro[1,3-thiazino][3,4-b]isoquinolinium iodide (1.05 g) is thus obtained.

(RS)-1,6,11,11a-Tetrahydro[1,3-thiazino][3,4-b]isoquinoline-4-thione can be prepared in the following manner:

A solution of (RS)-3-(2-hydroxyethyl)-1,2,3,4-tetrahydroisoquinoline (3.1 g) in pyridine (15 cc) is added dropwise, whilst stirring and at a temperature of about −10° C., to a solution of triethylamine (5.3 cc) and carbon disulphide (3 cc) in pyridine (10 cc); the reaction mixture is kept at the same temperature for 17 hours. A solution of methanesulphonyl chloride (1.35 cc) in pyridine (10 cc) is then added dropwise and the reaction mixture is left to stand for 2 hours until a temperature of about 20° C. is reached. Dimethylformamide (100 cc) is added to the reaction mixture and the whole is evaporated to dryness at 80° C. under reduced pressure (20 mm Hg).

The residue is chromatographed on silica gel (60 g) contained in a column 2 cm in diameter, elution being carried out with methylene chloride and fractions (200 cc) being collected. Fractions 2 to 5 are combined and evaporated to dryness under reduced pressure (40 mm Hg) at 30° C. (RS)-1,6,11,11a-Tetrahydro[1,3-thiazino][3,4-b]isoquinoline-4-thione (0.68 g) is thus obtained in the form of white crystals melting at 162° C.

EXAMPLE 4

(RS)-3-(2-Hydroxyethyl)-N-(3-methylisoquinol-5-yl)-1,2,3,4-tetrahydroisoquinoline-2-carbothioamide (16.5 g) is heated in 6 N hydrochloric acid (165 cc) for 30 minutes at 100° C. After cooling, the solution obtained is rendered alkaline by addition of 10 N sodium hydroxide solution (100 cc) and extraction is then carried out with methylene chloride (3×200 cc). The organic extracts are combined, washed with water (200 cc) and then dried over magnesium sulphate, filtered and concentrated to dryness at 40° C. under reduced pressure (25 mm Hg). The residue crystallises on cooling; it is recrystallised from a mixture of diisopropyl ether (250 cc) and acetonitrile (130 cc). (RS)-4-[(3-Methylisoquinol-5-yl)imino]-1,6,11,11a-tetrahydro[1,3-thiazino][3,4-b]-isoquinoline (9.0 g) is thus obtained in the form of white crystals melting at 158° C.

(RS)-3-(2-Hydroxyethyl)-N-(3-methylisoquinol-5-yl)-1,2,3,4-tetrahydroisoquinoline-2-carbothioamide can be prepared in the following manner:

5-Isothiocyanato-3-methylisoquinoline (8.8 g) is added to a solution of (RS)-3-(2-hydroxyethyl)-1,2,3,4-tetrahydroisoquinoline (7.8 g) in ethanol (150 cc). A white precipitate rapidly forms. After stirring for 17 hours at a temperature of about 20° C., the mixture is evaporated to dryness at 40° C. under reduced pressure (30 mm Hg). (RS)-3-(2-Hydroxyethyl)-N-(3-methylisoquinol-5-yl)-1,2,3,4-tetrahydroisoquinoline-2-carbothioamide (16.5 g) is thus obtained in the form of pale yellow crystals.

(RS)-3-(2-Hydroxyethyl)-1,2,3,4-tetrahydroisoquinoline (m.p. 63°–65° C.) can be prepared from (RS)-3-hydroxymethyl-1,2,3,4-tetrahydroisoquinoline in accordance with the method described by T. A. Crabb et al., J. C. S. Perkin II, 370 (1977).

5-Isothiocyanato-3-methylisoquinoline can be prepared in the following manner:

A solution of 5-amino-3-methylisoquinoline (20.0 g) in pyridine (300 cc) is added dropwise, whilst stirring and at a temperature of about −10° C., to a solution of triethylamine (14.0 g) and carbon disulphide (600 cc) in pyridine (50 cc). The reaction mixture is kept at −10° C. for 17 hours and a solution of N,N'-dicyclohexylcarbodiimide (28.6 g) in pyridine (50 cc) is then added dropwise. Stirring is continued for 2 hours, whilst keeping the temperature at −10° C., and then for 15 hours at a temperature changing from −10° C. to 20° C. The reaction mixture is evaporated to dryness at 60° C. under reduced pressure (20 mm Hg). The solid residue is taken up in methylene chloride (350 cc); the insoluble material is filtered off and the filtrate is evaporated to dryness at 40° C. under reduced pressure (20 mm Hg). The deep red residue obtained is suspended, whilst stirring for 15 minutes, in diisopropyl ether (500 cc); the insoluble material is filtered off and the filtrate is evaporated to dryness under reduced pressure (20 mm Hg) at 40° C.

This residue is chromatographed on silica gel (250 g) contained in a column 5.5 cm in diameter, elution being carried out successively with methylene chloride (2000 cc), a mixture (98-2) of methylene chloride and methanol (1000 cc) and a mixture (95-5) of methylene chloride and methanol (500 cc), and the eluate being collected in fractions (100 cc). Fractions 12 to 34 are combined and evaporated to dryness under reduced pressure (30 mm Hg) at 40° C. The residue crystallises on cooling; the crystals are washed with diisopropyl ether (50 cc). 5-Isothiocyanato-3-methylisoquinoline (21.1 g), melting at 92° C., is thus obtained.

EXAMPLE 5

By following the procedure of Example 1 but starting with (RS)-3-(2-hydroxyethyl)-N-(3-propylisoquinol-5-yl)-1,2,3,4-tetrahydroisoquinoline-2-carbothioamide (4.3 g) in 6 N hydrochloric acid (50 cc), (RS)-4-[(3-propylisoquinol-5-yl)imino]-1,6,11,11a-tetrahydro[1,3-thiazino][3,4-b]isoquinoline (2.9 g) is obtained in the amorphous form. It is dissolved in absolute ethanol (about 10 cc), and fumaric acid (0.8 g) is added. The white crystals which have appeared are isolated by filtration and washed with diethyl ether. (RS)-4-[(3-Propylisoquinol-5-yl)imino]-1,6,11,11a-tetrahydro[1,3-thiazino][3,4-b]-isoquinoline (3.2 g) is thus obtained in the form of the neutral fumarate which melts at 145° C.

(RS)-3-(2-Hydroxyethyl)-N-(3-propylisoquinol-5-yl)-1,2,3,4-tetrahydroisoquinoline-2-carbothioamide can be prepared in the following manner:

5-Isothiocyanato-3-propylisoquinoline (4.5 g) is added to a solution of (RS)-3-(2-hydroxyethyl)-1,2,3,4-tetrahydroisoquinoline (3.5 g) in absolute ethanol (35 cc). After stirring for 20 hours at a temperature of about 20° C., the crystals which have appeared are filtered off and then washed with ethanol (2×2 cc). (RS)-3-(2-Hydroxyethyl)-N-(3-propylisoquinol-5-yl)-1,2,3,4-tetrahydroisoquinoline-2-carbothioamide (5.7 g) is thus obtained; after recrystallisation from propanol (50 cc), it melts at 175° C.

5-Isothiocyanato-3-propylisoquinoline can be prepared from 5-amino-3-propylisoquinoline in accordance with the method hereinbefore described for the preparation of isothiocyanates of general formula IV wherein A is a 3-alkylisoquinol-5-yl radical using 5-aminoisoquinolines of general formula V as starting materials.

EXAMPLE 6

By following the procedure of Example 1 but starting with (RS)-3-(2-hydroxyethyl)-N-(3-octylisoquinol-5-yl)-1,2,3,4-tetrahydroisoquinoline-2-carbothioamide (23.8 g) in 6 N hydrochloric acid (250 cc), (RS)-4-[(3-octylisoquinol-5-yl)imino]-1,6,11,11a-tetrahydro[1,3-thiazino][3,4-b]isoquinoline (9.5 g) is obtained in the form of an oil. It is dissolved in absolute ethanol (50 cc), and a hot solution of fumaric acid (1.2 g) in ethanol (100 cc) is added. After cooling, the crystals which have appeared are isolated by filtration and a first fraction is thus obtained. The mother liquors are evaporated to dryness at 60° C. under reduced pressure (20 mm Hg) and the residue is taken up in hot isopropanol (80 cc). After cooling to about 20° C., crystals appear and are isolated by filtration; a second fraction is thus obtained which is combined with the first.

After recrystallisation of the combined fractions from isopropanol (100 cc), (RS)-4-[(3-octylisoquinol-5-yl)imino]-1,6,11,11a-tetrahydro[1,3-thiazino][3,4-b]-isoquinoline (5.0 g) is obtained in the form of the acid fumarate as yellow crystals which melt at 144° C.

(RS)-3-(2-Hydroxyethyl)-N-(3-octylisoquinol-5-yl)-1,2,3,4-tetrahydroisoquinoline-2-carbothioamide can be prepared in the following manner:

5-Isothiocyanato-3-octylisoquinoline (14.9 g) is added to a solution of (RS)-3-(2-hydroxyethyl)-1,2,3,4-tetrahydroisoquinoline (8.9 g) in absolute ethanol (200 cc). After stirring for 30 hours at a temperature of about 20° C., the mixture is evaporated to dryness at 40° C. under reduced pressure (20 mm Hg).

(RS)-3-(2-Hydroxyethyl)-N-(3-octylisoquinol-5-yl)-1,2,3,4-tetrahydroisoquinoline-2-carbothioamide (23.8 g) is thus obtained in the form of an oil.

5-Isothiocyanato-3-octylisoquinoline can be prepared from 5-amino-3-octylisoquinoline in accordance with the method hereinbefore described for the preparation of isothiocyanates of general formula IV wherein A is a 3-alkylisoquinol-5-yl radical using 5-aminoisoquinolines of general formula V as starting materials.

The present invention includes within its scope pharmaceutical compositions comprising, as active ingredient, at least one of the compounds of general formula I, or a non-toxic acid addition salt thereof, in association with a pharmaceutical carrier or coating. The invention includes especially such preparations made up for oral, parenteral or rectal administration or as ointments.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration also include capsules of absorbable material such as gelatin containing the active substance with or without the addition of diluents or excipients.

Preparations according to the invention for parenteral administration include sterile suspensions and emulsions and non-aqueous solutions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilising agents, by irradiation, or by heating. They may also be manufactured in the form of sterile solid compositions, which can be dissolved in a sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. The compositions are particularly useful in human therapy by virtue of their anti-inflammatory, analgesic and antipyretic action. They are particularly indicated for the treatment of inflammatory diseases (ankylosing spondylarthritis, acute articular rheumatism and arthrosis), acute and chronic pains, rheumatic and traumatic algias, dental, neurological and visceral pains, various algias (pains experienced by cancer patients), febrile conditions, and medical, surgical and obstetrical complaints giving rise to thromboses and embolisms.

In human therapy, the doses depend on the desired effect and the duration of the treatment; they are generally between 100 and 1500 mg per day for an adult.

In general, the physician will decide the posology considered most appropriate, taking into account the age, weight and other factors intrinsic to the patient being treated.

The following Example illustrates pharmaceutical compositions according to the invention.

EXAMPLE 7

Tablets containing doses (100 mg) of active product and having the following composition are prepared in accordance with the usual technique:
(RS)-4-[(3-methylisoquinol-5-yl)imino]-1,6,11,11a-tetrahydro[1,3-thiazino][3,4-b]-

| | |
|---|---|
| isoquinoline | 0.100 g |
| starch | 0.110 g |
| precipitated silica | 0.035 g |
| magnesium stearate | 0.005 g. |

We claim:

1. An isoquinoline derivative of the formula:

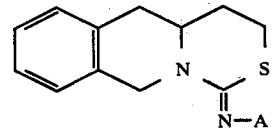

wherein A represents pyrid-3-yl, isoquinol-5-yl or a 3-alkylisoquinol-5-yl radical in which the alkyl moiety contains 1 to 10 carbon atoms, and pharmaceutically acceptable acid addition salts thereof.

2. An isoquinoline derivative according to claim 1 wherein A represents a 3-alkylisoquinol-5-yl radical in which the alkyl moiety contains 1 to 10 carbon atoms, and pharmaceutically acceptable acid addition salts thereof.

3. An isoquinoline derivative according to claim 1 wherein A represents isoquinol-5-yl, or a 3-alkylisoquinol-5-yl radical in which the alkyl moiety contains 1 to 8 carbon atoms, and pharmaceutically acceptable acid addition salts thereof.

4. An isoquinoline derivative according to claim 1 wherein A represents isoquinol-5-yl or 3-methylisoquinol-5-yl, and pharmaceutically acceptable acid addition salts thereof.

5. An isoquinoline derivative according to claim 1 which is (RS)-4-(isoquinol-5-ylimino)-1,6,11,11a-tetrahydro[1,3-thiazino][3,4-b]isoquinoline, and pharmaceutically acceptable acid addition salts thereof.

6. An isoquinoline derivative according to claim 1 which is (RS)-4-[(3-methylisoquinol-5-yl)imino]-1,6,11,11a-tetrahydro[1,3-thiazino][3,4-b]isoquinoline, and pharmaceutically acceptable acid addition salts thereof.

7. An isoquinoline derivative according to claim 1 which is (RS)-4-(pyrid-3-ylimino)-1,6,11,11a-tetrahydro[1,3-thiazino][3,4-b]isoquinoline, and pharmaceutically acceptable acid addition salts thereof.

8. An isoquinoline derivative according to claim 1 which is (RS)-4-[(3-propylisoquinol-5-yl)imino]-

1,6,11,11a-tetrahydro[1,3-thiazino][3,4-b]isoquinoline, and pharmaceutically acceptable acid addition salts thereof.

9. An isoquinoline derivative according to claim 1 which is (RS)-4-[(3-octylisoquinol-5-yl)imino]-1,6,11,11a-tetrahydro[1,3-thiazino][3,4-b]isoquinoline, and pharmaceutically acceptable acid addition salts thereof.

10. A pharmaceutical composition which comprises, as active ingredient, an isoquinoline derivative as claimed in claim 1, or a pharmaceutically acceptable acid addition salt thereof, in association with at least one compatible pharmaceutically acceptable carrier.

* * * * *